(12) United States Patent
Stewart et al.

(10) Patent No.: US 10,039,502 B2
(45) Date of Patent: Aug. 7, 2018

(54) ELECTROPHYSIOLOGICAL SIGNAL PROCESSING AND UTILIZATION

(75) Inventors: Mark T. Stewart, Lino Lakes, MN (US); Scott W. Davie, Beaconsfield (CA); Giles Desrochers, Beaconsfield (CA)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1051 days.

(21) Appl. No.: 13/084,853

(22) Filed: Apr. 12, 2011

(65) Prior Publication Data
US 2012/0265084 A1 Oct. 18, 2012

(51) Int. Cl.
| | | |
|---|---|---|
| *A61B 5/05* | (2006.01) |
| *A61B 5/00* | (2006.01) |
| *A61B 5/0402* | (2006.01) |
| A61B 5/042 | (2006.01) |
| A61B 6/12 | (2006.01) |
| A61B 6/00 | (2006.01) |
| A61B 8/08 | (2006.01) |
| A61B 5/01 | (2006.01) |
| A61B 5/0215 | (2006.01) |

(Continued)

(52) U.S. Cl.
CPC ............ *A61B 5/743* (2013.01); *A61B 5/0402* (2013.01); *A61B 5/01* (2013.01); *A61B 5/0215* (2013.01); *A61B 5/0422* (2013.01); *A61B 5/055* (2013.01); *A61B 5/14542* (2013.01); *A61B 5/6852* (2013.01); *A61B 6/12* (2013.01); *A61B 6/503* (2013.01); *A61B 8/0841* (2013.01); *A61B 8/0883* (2013.01)

(58) Field of Classification Search
CPC .......... A61B 2017/00053; A61B 8/466; A61B 5/0205; A61B 5/0422; A61B 5/0402; A61B 5/743
USPC .................................. 600/424, 523
See application file for complete search history.

(56) References Cited

U.S. PATENT DOCUMENTS

| | | |
|---|---|---|
| 7,225,014 B1 | 5/2007 | Province |
| 7,774,051 B2 | 8/2010 | Voth |

(Continued)

FOREIGN PATENT DOCUMENTS

| | | |
|---|---|---|
| CN | 2897151 Y | 5/2007 |
| CN | 101443792 A | 5/2009 |

(Continued)

OTHER PUBLICATIONS

International Search Report and Written Opinion dated Jul. 3, 2012, for corresponding International Application No. PCT/US2012/033171; International Filing Date: Apr. 12, 2012 consisting of 11-pages.

(Continued)

*Primary Examiner* — Michael D Abreu
(74) *Attorney, Agent, or Firm* — Christopher & Weisberg, P.A

(57) ABSTRACT

A method of mapping electrophysiological information, including receiving imaging information for a tissue region; receiving a monophasic action potential signal from the tissue region; assigning a value corresponding to a depolarization segment of the monophasic action potential signal; receiving location information associated with the monophasic action potential signal; and generating an image based on the imaging information, the assigned value, and the location information.

23 Claims, 7 Drawing Sheets

(51) Int. Cl.
*A61B 5/055* (2006.01)
*A61B 5/145* (2006.01)

(56) References Cited

U.S. PATENT DOCUMENTS

| | | |
|---|---|---|
| 7,831,076 B2 | 11/2010 | Altmann et al. |
| 7,831,294 B2 | 11/2010 | Viswanathan |
| 2004/0078036 A1* | 4/2004 | Keidar .......................... 606/41 |
| 2004/0097806 A1 | 5/2004 | Hunter et al. |
| 2005/0203375 A1* | 9/2005 | Willis et al. ................. 600/407 |
| 2007/0073179 A1* | 3/2007 | Afonso et al. ............... 600/523 |
| 2010/0067755 A1 | 3/2010 | Chan et al. |
| 2010/0094274 A1 | 4/2010 | Narayan et al. |
| 2010/0274123 A1 | 10/2010 | Voth |
| 2011/0028820 A1 | 2/2011 | Lau et al. |
| 2012/0022384 A1* | 1/2012 | Teixeira ....................... 600/509 |

FOREIGN PATENT DOCUMENTS

| | | |
|---|---|---|
| EP | 1421913 A1 | 5/2004 |
| WO | 0042914 A1 | 7/2000 |
| WO | 2005072607 A1 | 8/2005 |
| WO | 2008118992 A1 | 10/2008 |

OTHER PUBLICATIONS

Notice on the First Office Action of the People's Republic of China, including Search Report dated Feb. 4, 2015, or corresponding Application No. 201280027415.7, Application Date: Apr. 12, 2012 consisting of 24 pages.

\* cited by examiner

ELECTROPHYSIOLOGICAL SIGNAL PROCESSING AND UTILIZATION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates generally to medical systems and methods of use thereof, and more particularly to obtaining, processing and displaying electrophysiological information for clinical use.

BACKGROUND OF THE INVENTION

In modern medicine, a considerable number of interventional procedures have been developed and typically require physiologic monitoring of a patient using various imaging techniques and diagnostic instrumentation. Indeed, image guided procedures employing visual displays to guide and assist a physician operator are commonplace in the interventional laboratories and operating theaters. A variety of instrumentation modalities provide images to guide interventional procedures. In some situations, images are acquired prior to the interventional procedure or treatment. Other approaches involve acquiring images at the beginning of the procedure, while still some other procedures involve the acquisition of data in real-time.

Commonly used instrumentation modalities used to image patient anatomy and physiology include 1) X-ray (radiation transmitted through a body and received with a sensor to produce an image), 2) fluoroscopy (an x-ray variant with dynamic imaging), 3) computerized tomography ("CT"), 4) magnetic resonance imaging ("MRI"), and 5) acoustics/echo.

In addition to imaging, various physiological parameters are often monitored during an interventional procedure. For example, such physiological monitoring may include the use of an electrocardiogram, blood pressure monitoring, blood oxygenation sensors, etc. For electrophysiological applications, electrical activity in a designated tissue area, such as the heart, may be monitored or recorded to aid a physician in diagnosing and/or treating a patient. Such electrograms corresponding to underlying physiological mechanisms or morphologies may provide a wealth of information for such diagnoses and treatment.

Combining imaging capacity with electrophysiological information in an easily accessible, informative presentation to the physician benefits diagnosis and treatment efforts, and accordingly, there is an ongoing need to provide improvements in both the presentation of such information, as well as processing methodology and correlation to clinically-relevant conditions to provide enhanced information about the characteristics or behavior of a particular treatment or diagnosis site.

SUMMARY OF THE INVENTION

The present invention advantageously provides systems and methods of use thereof providing electrophysiological information in an easily accessible, informative presentation to the physician to benefit diagnosis and treatment efforts, as well as processing methodology and correlation to clinically-relevant conditions to provide enhanced information about the characteristics or behavior of a particular treatment or diagnosis site.

In particular, a method of displaying electrophysiological information is provided, including obtaining a three-dimensional rendering of an anatomical region; obtaining a monophasic action potential signal; calculating a value associated with a depolarization segment of the monophasic action potential signal; and displaying a graphical indicator of the value on the rendering of the anatomical region. The three-dimensional rendering may be generated using electric potential-based navigation, and the electric potential-based navigation may include tracking one or more electrodes in three-dimensional space in proximity to the anatomical region. Calculating the value associated with the depolarization segment may include calculating a time duration; calculating an upstroke velocity; calculating a maximum amplitude value; and/or calculating a time duration for the monophasic action potential signal to recede to a predetermined percentage of the maximum amplitude value. The method may include identifying a tissue structure based at least in part on the calculated value. Obtaining the monophasic action potential signal may include contacting the anatomical region with a medical device and generating a contact status indication based at least in part on the calculated value. The method may include obtaining an electrocardiogram signal; comparing at least a portion of the monophasic action potential signal to at least a portion of the electrocardiogram signal; and generating an alert based at least in part on the comparison; for example, comparing at least a portion of the monophasic action potential signal to the electrocardiogram signal may include comparing a portion of the monophasic action potential signal to at least one of a P, QRS, and T-wave portion of the electrocardiogram signal. The graphical indicator may include a color assigned to the value, and/or the method may include generating a graphical treatment indicator on the rendering based at least in part on the calculated value, the graphical treatment indicator providing a suggested treatment location.

A method of mapping electrophysiological information is provided, including receiving imaging information for a tissue region; receiving a monophasic action potential signal from the tissue region; assigning a value corresponding to a depolarization segment of the monophasic action potential signal; receiving location information associated with the monophasic action potential signal; and generating an image based on the imaging information, the assigned value, and the location information. Receiving imaging information for a tissue region may include acquiring three-dimensional electric potential information. Receiving a monophasic action potential signal from the tissue region may include obtaining a monophasic action potential signal with a medical device proximate to the tissue region. Receiving location information associated with the monophasic action potential signal may include obtaining location information of the medical device. Generating an image may include displaying a three-dimensional rendering of the tissue region, and the rendering may include a color variation indicating the assigned value at a location on the rendering corresponding to the received location information. The rendering may also include a color variation indicating a suggested location for treatment.

A medical system is provided, including a display; a control unit in communication with the display, the control unit programmed to: receive a monophasic action potential signal, receive three-dimensional location information associated with the monophasic action potential signal, calculate a value corresponding to a depolarization segment of the monophasic action potential signal, and generate an image based on the three-dimensional location information and the calculated value. The control unit may be programmed to: obtain an electrocardiogram signal; compare at least a portion of the monophasic action potential signal to at least a portion of the electrocardiogram signal; and generate an alert based at least in part on the comparison. The system may include a medical device in communication with the control unit, the medical device including a plurality of electrodes; and/or an image acquisition device in communication with the control unit.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
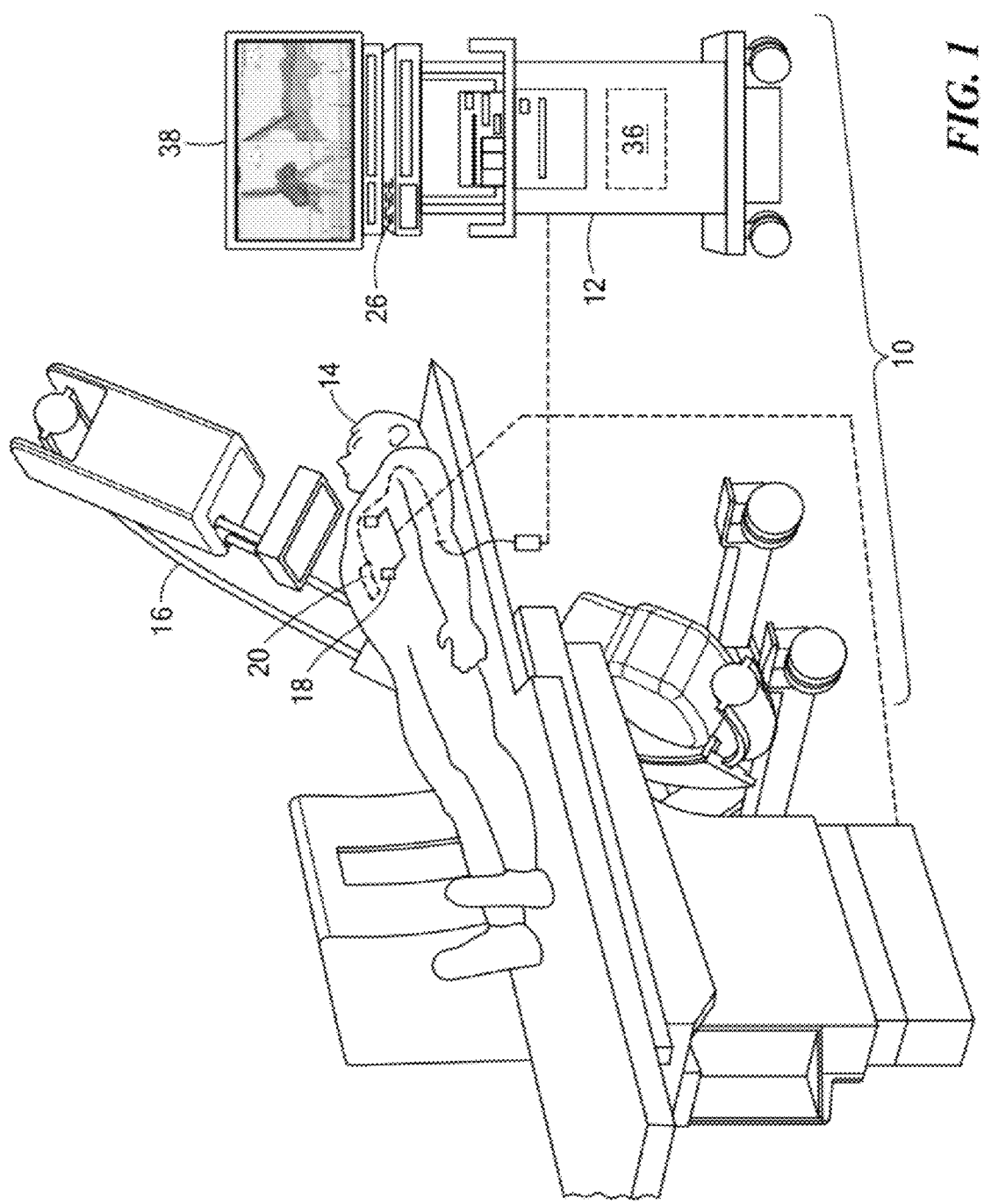
FIG. 1 is an illustration of an example of a medical system constructed in accordance with the principles of the present invention.

The present disclosure provides systems and methods of use thereof providing electrophysiological information in an easily accessible, informative presentation to the physician to benefit diagnosis and treatment efforts, as well as processing methodology and correlation to clinically-relevant conditions to provide enhanced information about the characteristics or behavior of a particular treatment or diagnosis site. Now referring to the drawings in which like reference designators refer to like elements there is shown in FIG. 1 an embodiment of a medical system referred to generally as "10." The system 10 may generally include a system control/processing unit 12 and one or more devices operable to acquire, measure, monitor or otherwise convey information regarding a patient 14 to the control unit 12 and vice versa.

For example, the system 10 may include one or more image capture or acquisition devices 16 external to the patient 14 and in communication with the control unit 12. Examples of such image capture and acquisition devices 16 may include an X-ray, fluoroscopic, or computed tomography ("CT") device. The image acquisition device(s) 16 may also include, for example, a magnetic resonance imaging ("MRI") device, an ultrasound/acoustic device, or the like that capture, measure, or otherwise obtain anatomical information (e.g., information regarding a structure of the patient) and/or physiological information (e.g., information regarding processes, functions, conditions, or activities) of the patient 14 for imaging purposes. The image capture or acquisition devices 16 may also include a three-dimensional electric potential monitoring/recording system, such as the LocaLisa® navigation system from Medtronic, Inc. Action potential information is recorded with respect to an electrode in proximity to or in contact with an anatomical region of interest. The electrode(s) are then moved around in the region of interest while the electric field strength is measured in three different field vectors to create a rendered 3-D surface of the targeted portion of anatomy, such as a heart chamber.

The system 10 may include one or more physiological assessment devices 18 coupled to or positionable about an exterior of the patient 14 and in communication with the control unit 12. The one or more physiological assessment devices 18 generally measures, monitors or records a physiologic state or condition of the patient 14. For example, the physiological monitoring device(s) 18 may include one or more electrodes or sensors placed on an exterior of the patient 14 to record an electrogram ("EGM") of electrical activity on or about a portion of the patient 14. As used herein, the term electrogram is referred to as a recording or measurement of changes in electric potential. A specific example of an electrogram may be the recording and/or processing of an electrocardiogram ("ECG") signal trace using a plurality of electrodes or leads placed on the skin of the patient 14. Various other electrograms may also be obtained by the physiological monitoring/measuring device 18, including, for example, intracardiac electrograms indicative of an arrhythmia loci, electric potential changes in a particular chamber of the heart or in proximity to the His bundle, esophageal electrograms, or the like. Other examples of physiological assessment devices 18 may include (but are not limited to) blood oxygenation measuring devices, blood pressure measurement devices, blood flow measuring devices (e.g., a device measuring or monitoring flow direction and magnitude, Doppler ultrasound, etc.), temperature monitoring devices, and/or respiration/respiratory rate monitoring devices.'

The system 10 may include one or more minimally-invasive or interventional medical device(s) 20 positionable within a portion of the patient 14 to acquire anatomical or physiological information, or to otherwise diagnose or treat the patient 14. The medical device(s) 20 may be coupled to the control unit 12, which may communicate operational procedures and protocols dictating the operation of the medical device 20 as well as receiving feedback from the medical device 20 regarding the designated procedure, treatment, or the like with respect to the patient 14. The medical device(s) 20 may include a catheter having one or more diagnostic or treatment elements that is insertable into the patient 14 through a small incision and routed to a desired region of the patient 14 through a vascular channel, for example. The treatment elements on the catheter may include, for example, one or more temperature, pressure, and/or electrical activity sensors facilitating information acquisition, diagnoses, or treatment procedures. An example of the medical device 20 may include an endoscope having a video capture assembly on it to obtain images of an internal region of the patient 14. Other specific examples of the medical device 20 may include pacing catheters, ablation catheters, or fluid delivery catheters (e.g., to deliver pharmaceutical compounds, imaging contrast fluids, etc.). The medical device(s) 20 may be operable to obtain one or more electrograms from an interior of the patient 14, as well as blood pressure, temperature, oxygenation, and the like described above.

Figure 2:
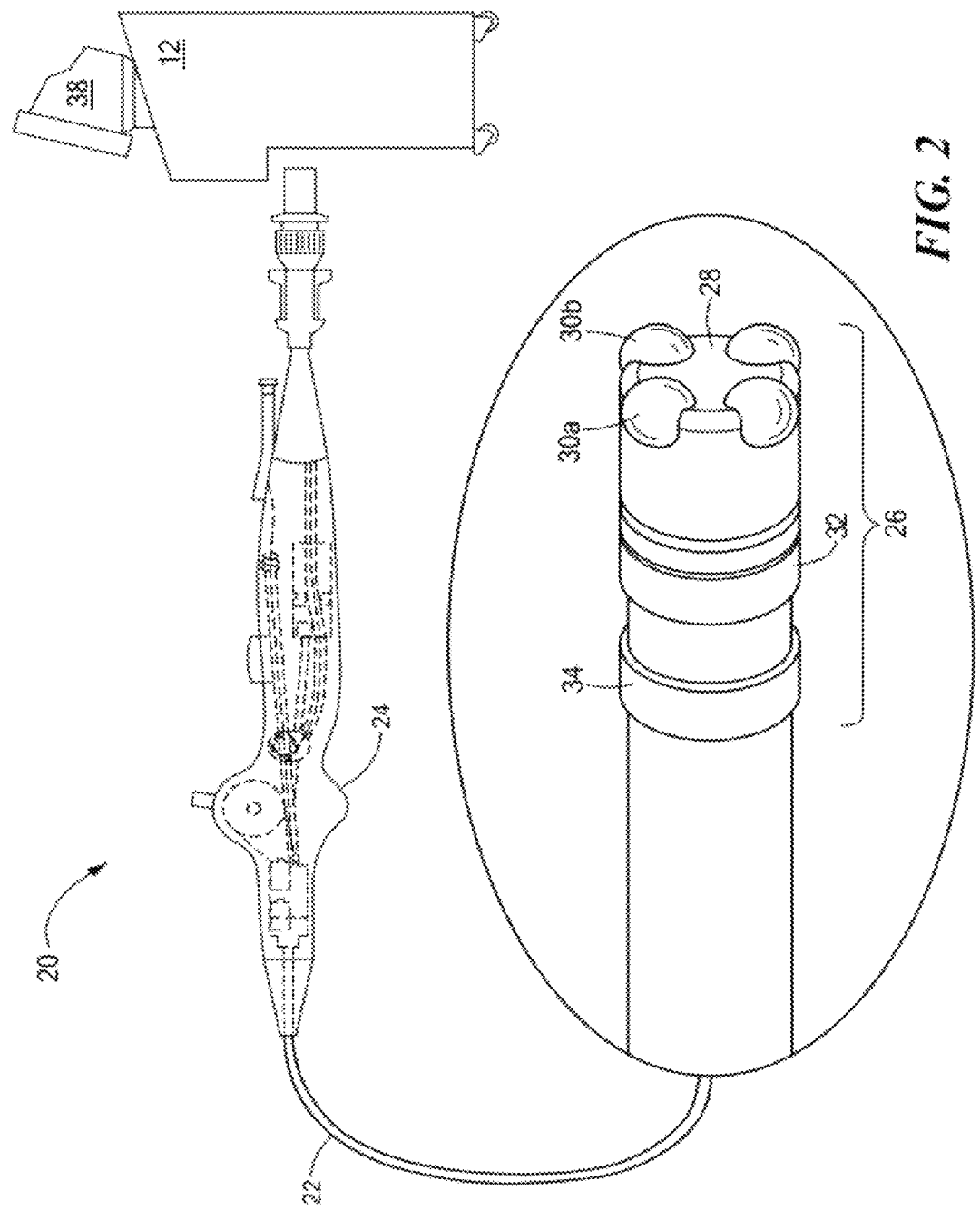
FIG. 2 is an additional illustration of the system in FIG. 1.

Referring now to FIG. 2, a particular example of the medical device 20 is shown. The medical device 20 may include an elongate body or shaft 22 with proximal and distal portions. The shaft 22 may be both flexible and resilient, with sufficient column strength facilitating steady contact with tissue to improve signal fidelity in diagnosing contacted tissue as well as improve therapeutic thermal exchange between the device 20 and contacted tissue for particular applications. The medical device 20 may further include a handle 24 affixed to the proximal portion of the shaft 22.

The device 20 may further include a treatment and/or diagnosis assembly 26 coupled to the distal portion of the shaft 22. The treatment/diagnosis assembly 26 may include a distal tip or dome housing 28 and an array of electrodes (30a, 30b . . . collectively referred to as '30') for measuring or detecting electrical activity or signals, such as a monophasic action potential. The electrodes 30 may have a partially spherical surface with a relatively small outer diameter, such as outer diameters of about one-half to two millimeters. In one example they may have a diameter of one millimeter. While the first array is illustrated as containing four electrodes, one or more electrodes in any suitable configuration may be implemented. The electrodes may be made of one or more non-polarizing materials, such as silver, silver chloride, platinum, iridium, titanium nitride, gold, stainless steel, aluminum, and alloys and combinations thereof for example, to improve the fidelity of detected or monitored signals.

The dome housing 28 may be made of various materials, including polymers or metals. If the dome housing 28 is made of a polymer, such as polyether-ether-ketone (PEEK), polysulfone, polyurethane, acetal, or other similar engineering plastic, it will have an electrically insulating effect to isolate the electrodes 30. Alternately, the dome housing 28 may be made of an electrically conductive material, for example selected from the group consisting of silver, silver chloride, platinum, iridium, gold, stainless steel, aluminum, and alloys and combinations thereof. If the dome housing 28 is made of metal, an insulating material such as one or more polymers may be provided between the dome housing 28 and the electrodes 30, and the dome housing 28 may further serve as a conduit for the delivery of radiofrequency ablation energy.

The medical device 20 may further include an auxiliary electrode 32 on the shaft 22 for determining a potential with relation to a corresponding potential obtained from the electrode array 30. The electrode 32 may be positioned a pre-determined distance proximal of the electrode array 30. A dedicated pacing electrode 34 may also be included for synchronizing the recorded or monitored signals from the electrode array to a local heartbeat. The auxiliary electrode 32 and pacing electrode 34 may have relatively smooth outer surfaces with minimal or no protrusion. The auxiliary electrode 32 and pacing electrode 34 may include substantially cylindrical bands surrounding or otherwise attached to the shaft 22 coaxial with a longitudinal axis, for example. These electrodes may be flush with the outer surface of the shaft 22, or may be recessed to reduce a possibility of direct or depolarizing contact with tissue. Alternatively, the auxiliary electrode 30 may be recessed, while the pacing electrode 32 may be larger to increase its exposure and contact with tissue to be paced.

The medical device may also include features to indicate where at least one component is currently positioned during the phases of a medical treatment. For example, the real-time location of the electrode array 30, as well as the auxiliary electrode 32 and the pacing electrode 34 may be indicated with one or more radiopaque or other trackable markers.

Referring again to FIG. 1, the control/processing unit 12 is coupled to one or more of the image capture or acquisition device(s) 16, physiological assessment devices 18, and/or interventional medical devices 20 described above. The control unit 12 may be used to receive and/or process information communicated from the attached devices 16, 18, 20 as well as send operational commands or signals to the devices during their use. For example, the control unit 12 may have suitable components for obtaining signals from the attached devices, and may also include one or more sensors to monitor operating parameters throughout the system, including for example, pressure, temperature, flow rates, volume, or similar measurements in the control unit 12 and/or the coupled devices.

The coupling and communication between the control unit 12 and the devices may be achieved through a direct wired connection or through wireless communication protocols as known in the art. The control unit 12 may include one or more controllers, processors, and/or software modules containing instructions or algorithms to provide for the automated operation and performance of the devices, features, sequences, calculations, or procedures described herein. The control unit 12 may include electronic storage media 36 retaining information regarding the operation of the control unit 12 and/or the devices 16, 18, 20, including stored anatomical and/or physiological information previously obtained from a patient 14.

The system 10 may include a display 38 in communication with the control unit 12 to provide visual information regarding the attached devices 16, 18, 20 and/or patient 14, as well as one or more user controls 40 facilitating operation of one or more aspects of the control unit 12 and the devices. The display 38 can include, for example, a cathode ray tube ("CRT"), liquid crystal display ("LCD"), or other visual interface generally including a plurality of pixels or segmented display elements for visualizing information from the control unit 12 and/or coupled devices. The display 38 may be touch-screen operable and may be removable or releasable from the control unit 12 for ease of use and view. Alternatively, the display 38 may be integrated with the control unit 12 in a portable tablet device.

The system 10 may further provide for the manipulation of designated images and/or information provided on the display 38. The selection, manipulation, processing, and/or visualization of the selected characteristics or configurations of the images and information on the display 38 may be achieved through manipulation of the user controls 40 and the programming/processing components of the control unit 12. Such selective manipulation may include adjusting, rotation, panning, or zooming selected portions of one or more images on the display 38.

Figure 3:
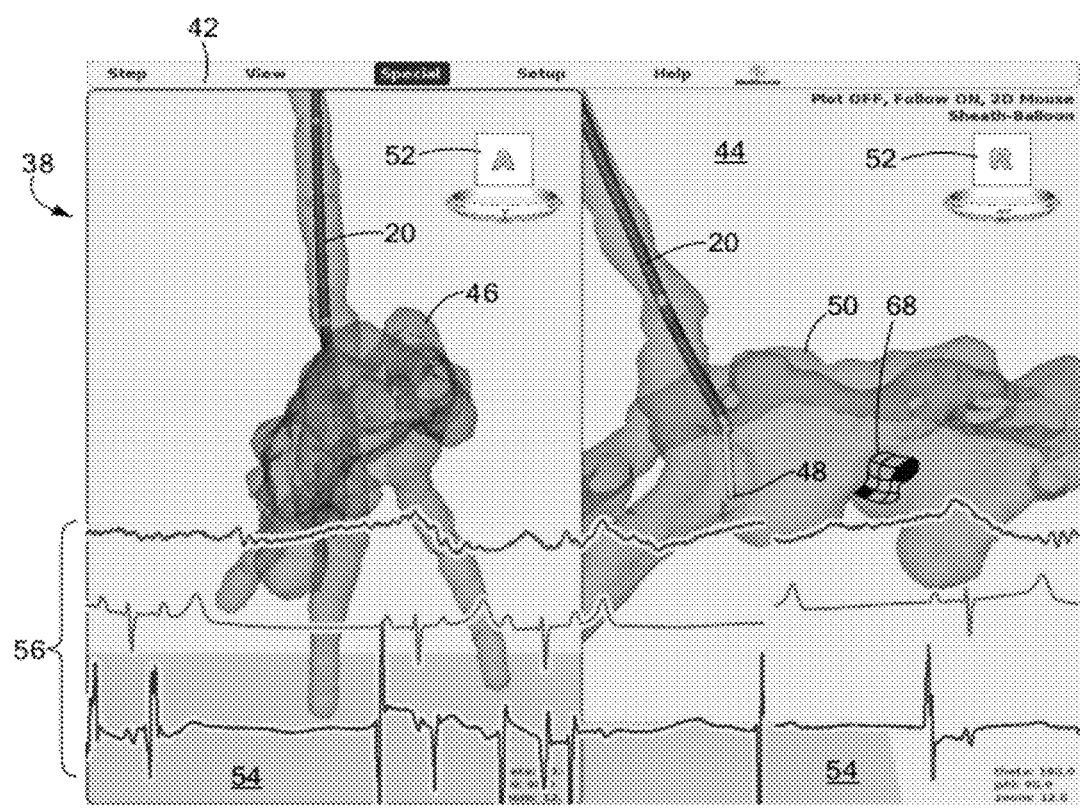
FIG. 3 is an illustration of an example of an image display of the system of FIG. 1.

Now referring to FIG. 3, an exemplary visual presentation of medical information on the display 38 is shown. The display 38 may generally include a menu bar 42 indicating available options and other selectable components related to the control unit 12, the display 38, and/or the coupled device(s) 16, 18, 20. The display 38 may further include a background 44 as a contrasting backdrop against which other images or information is displayed.

The display 38 may generally include a first plurality of pixels displaying a first image 46 produced at least in part from information received from one or more of the image acquisition devices 16, the physiological assessment devices 18, and/or the medical devices 20. The information resulting in the first image 46 may be acquired from the patient 14 and displayed in substantially real-time and/or displayed from previously-obtained information recalled from the storage media 36 of the control unit 12. The first image 46 may include a graphical reproduction or illustration of an anatomical structure or region of the patient 14, such as the heart, and may take up a substantial portion of the display 38 for ease of viewing and reference to an operator. The first image 46 may also include one or more medical devices 20 having one or more diagnostic and/or treatment elements 48 (such as those described above) in proximity to the displayed anatomical structure.

The display 38 may provide multiple images having different viewpoints or orientations of the same anatomical or physiological construct. For example, a second image 50 may be displayed with a second plurality of pixels, where the second image 50 is an alternative orientation of the first image 46. As shown in FIG. 3, the first image 46 may include an anterior-posterior view of the illustrated structure, while the second image 50 may include an illustration of the same anatomical structure in a right lateral view. Of course, other viewpoints may be provided on the display 38, and the display 38 may include a reference indicator or indicia 52 signifying the viewpoint from which the first and second images are shown. The display 38 may further include the illustration of a plane of reference 54 to aid a user in recognizing the illustrated orientation of the images at any given time. The imaged plane of reference 54 may be, for example, one of the customary sagittal, coronal, and/or transverse anatomical planes and may align with one of the physiological assessment device(s) 18, image capture device(s) 16 or medical device(s) 20.

The display 38 may also include a third plurality of pixels showing a third image 56 produced at least in part from information received from one or more of the image acquisition devices 16, the physiological assessment devices 18, and/or the medical devices 20. The third image 56 may include a graphical reproduction or illustration of one or more values corresponding to a physiological assessment, measurement, or monitored condition. For example, the third image 56 may include one or more signal traces or visual indicators corresponding to an ECG, EGM, blood pressure and/or oxygen concentration of the patient 14. The third image 56 may include an image or information related to instrumentation use or status. For example, the third image 56 may include one or more indications of treatment duration, information regarding expected or actual operational parameters of a one of the image acquisition devices 16, the physiological assessment devices 18, and/or the medical devices 20 (e.g., temperature measurements and thresholds of a device; electrical connection or sensor status and activity of a device, "ON" or "OFF", etc.). The third image 56 may consist of one or more signal traces or indications of the monitored or measured information, including a periodically-updated image or graphic that streams or sweeps across a portion of the display 38 as the information contributing to the third image 56 is updated or acquired.

The system 10 may be used to process and/or display anatomical and physiological information for a physician. Primarily, information sufficient to generate an image of a targeted tissue site or anatomical region of the patient 14 may be acquired from one or more of the image acquisition devices 16, the physiological assessment devices 18, the medical devices 20, and/or recalled from the storage media 36 of the control unit 12. Once the imaging information has been acquired or loaded from storage, the information may be processed by the control unit 12 to generate, for example, the first and/or second images 46, 50 on the display 38. As described above, the first and/or second images may include an anatomical structure and/or the positioning of a medical device. The system 10 may also generate the third image 56 on the display 38.

As described above, the third image 56 may include physiological and/or instrumentation information. The third image 56 may include one or more electrograms monitored or obtained at a designated site of the patient, such as a monophasic action potential ("MAP") signal from a cardiac region of the patient 14. A MAP signal may be obtained by placing an electrode, such as one of the electrodes 30 of medical device 20 for example, into contact with a tissue site. The medical device can be manipulated to apply local pressure from at least one electrode 30 to the tissue, causing local depolarization to obtain at least one MAP signal, which can be conveyed form the medical device 20 to the control unit 12.

Figure 4:
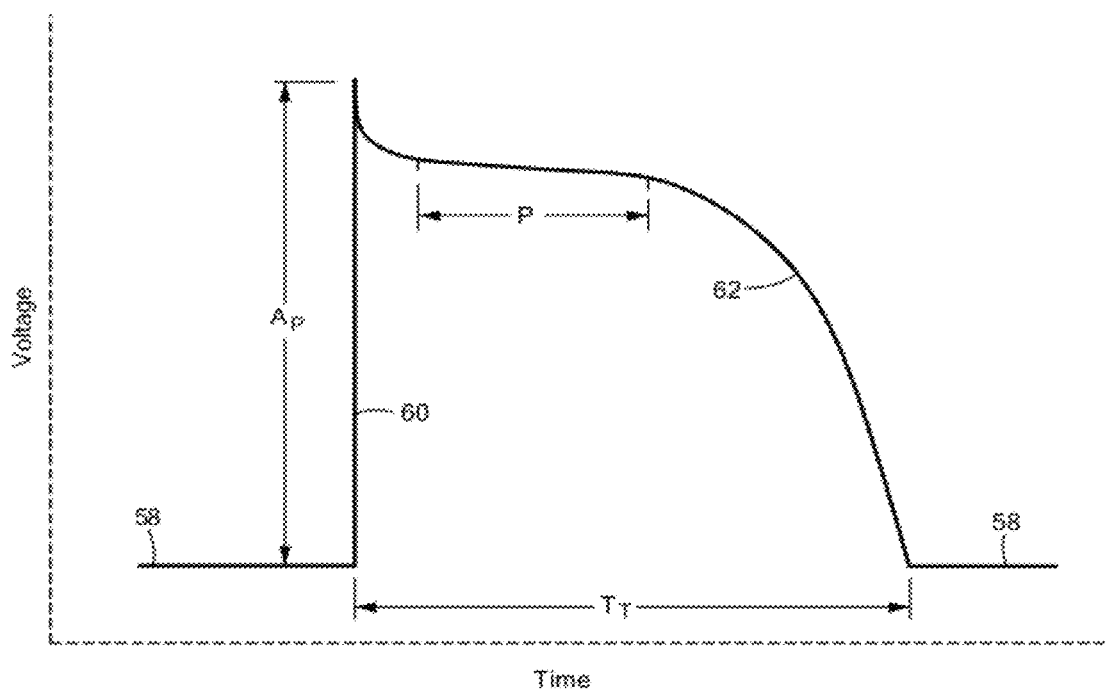
FIG. 4 is a diagram of an example of a monophasic action potential electrogram.

Turning to FIG. 4, an exemplary waveform of a monophasic action potential signal is shown. The waveform generally includes a resting potential 58, a depolarization segment 60 and a repolarization segment 62 indicating changes in transmembrane potential of the underlying cells over time due to ion influx and efflux. The system 10 may receive, process, and/or calculate a number of parameters or characteristics of an obtained or monitored MAP signal and present such information or indicators based on such information to an operating physician. For example, a MAP waveform may generally define a peak voltage amplitude $A_p$ and a time duration $T_{Ap}$ taken to reach the peak amplitude $A_p$. An associated upstroke velocity $V_{Ap}$ of the depolarization segment may be defined as the peak amplitude $A_p$ divided by the time duration $T_{Ap}$. The MAP waveform may also generally define a plateau "P" in the repolarization segment 62, and a difference between the voltage of the peak amplitude $A_p$ and the voltage at the plateau "P" may be calculated by the control unit 12. Additional timing and voltage characteristics of an obtained MAP signal may also be measured, processed or calculated by the control unit 12. For example, a total time duration $T_t$ extending from the initial depolarization and a return to baseline or resting potential may be calculated or measured. The timing associated with a voltage decay or drop as a percentage of the peak amplitude $A_p$ may also be measured or calculated, e.g., the time it takes for the voltage to drop to 90% of the peak amplitude $A_p$—$T_{90}$, or for other selected voltage percentage decreases—$T_\%$. Further, a refractory period or time duration between subsequent MAP signals or waveforms may be calculated, i.e., the time period between a repolarization segment reaching the resting potential and a following depolarization segment.

Figure 5:
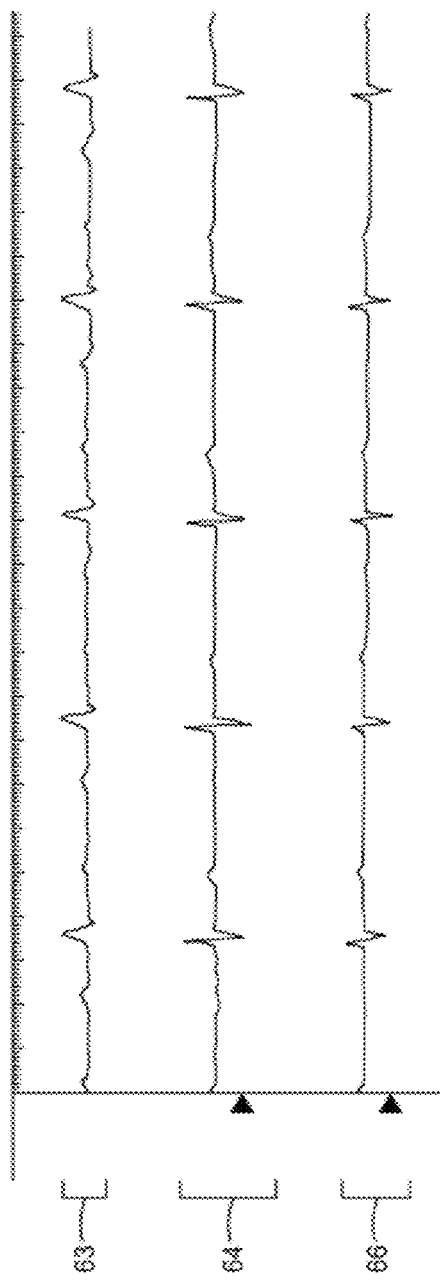
FIG. 5 is an illustration of a plurality of exemplary waveforms for use with the system of FIG. 1.

The control unit 12 may process, calculate, or otherwise measure a plurality of such MAP signal metrics and provide an indication of abnormal tissue morphology, specific anatomical structures or physiological functions, as well as provide a basis for assessing contact status and other operating parameters of the system 10. For example, FIG. 5 illustrates a plurality of signals including an electrocardiogram 63 and two electrogram signals 64, 66. Both electrogram signals 64, 66 indicate a depolarization segment or spike, but no plateau or other MAP signal characteristics (which the control unit 12 could analyze and conclude through an assessment of a difference between the voltage of the peak amplitude $A_p$ and the voltage at the plateau "P", or through calculating the total time duration $T_t$ extending from the initial depolarization and a return to baseline, for example, as compared to expected or pre-defined threshold values). These characteristics suggest that the tissue site may include inactive myocardial cells constituting scar tissue or ablated tissue, or that the contact between the medical device 20 and the tissue site is insufficient. Based on processing the parameters above, the control unit 12 may generate an alert to reposition the device or verify contact through imaging means, and/or visually designate the particular tissue region on the display with the concluded morphology resulting from the analysis of the MAP signal, as discussed in more detail below.

Figure 6:
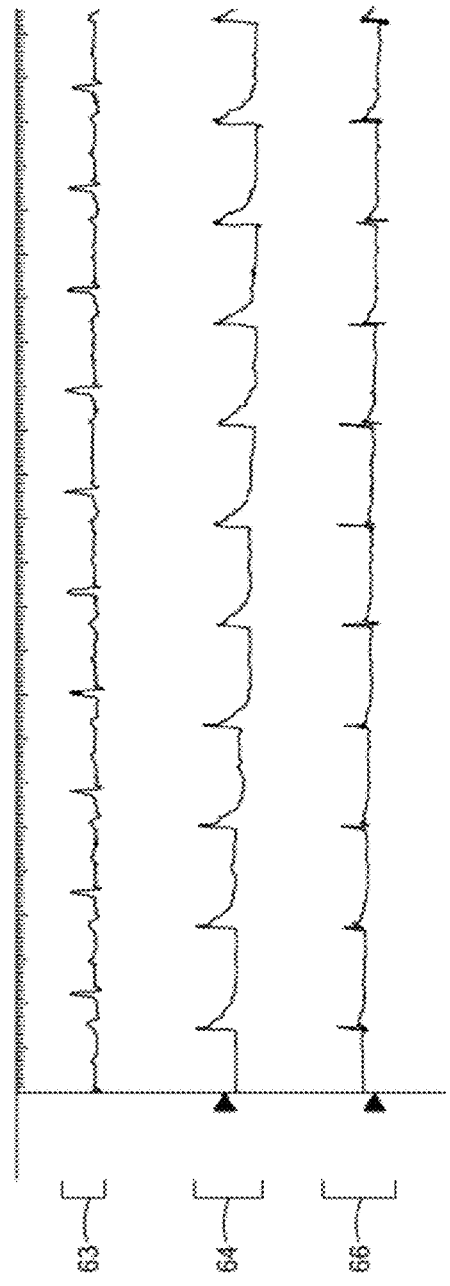
FIG. 6 is another illustration of a plurality of exemplary waveforms for use with the system of FIG. 1.
Figure 7:
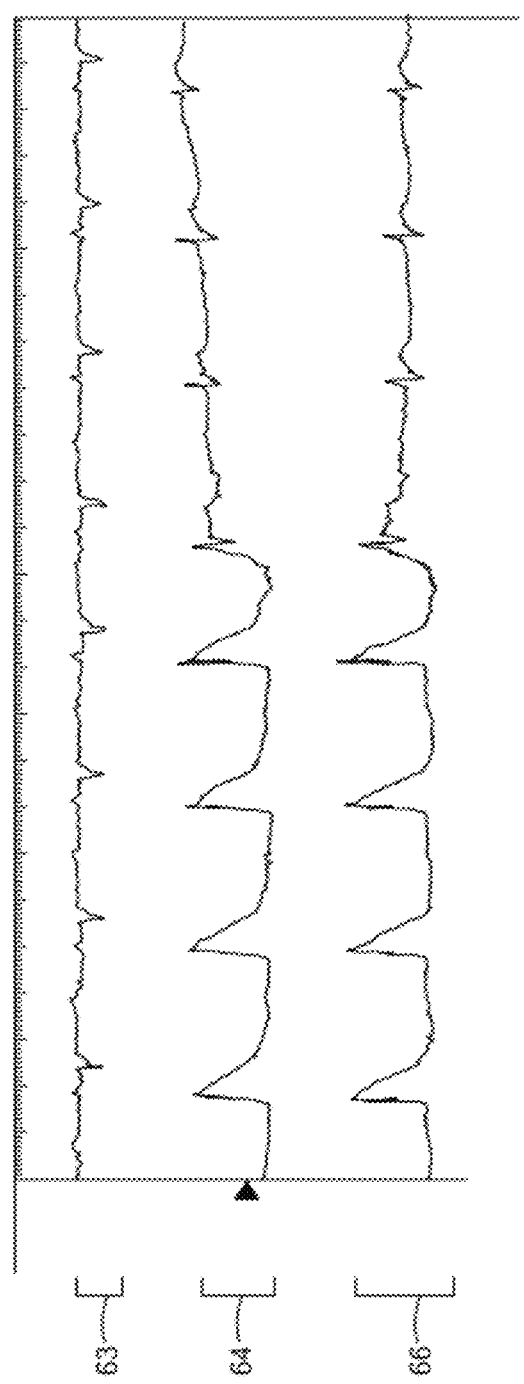
FIG. 7 is still another illustration of a plurality of exemplary waveforms for use with the system of FIG. 1.

Turning to FIG. 6, two signals are shown, where the first signal 64 includes greater MAP characteristics than a second signal 66. The control unit 12 may receive a plurality of MAP signals from one or more sources and, based on the analysis and processing of the parameters described herein, select one signal over another to show on the display 38 for an operator or physician, while additionally or alternatively generating an alert that the source or device obtaining the second signal 66 should be repositioned. In FIG. 7, the first and second signals 64, 66 initially display qualitative MAP characteristics, yet deteriorate into a different signal appearance. The control unit 12 may continuously assess the MAP signal parameters and generate an alert that sufficient contact with the tissue has been lost should any such change in signal occur.

MAP signal characteristics may also be used to differentiate tissue structures. For example, MAP signals obtained from pacemaker cells such as the sinus node differ from the MAP signals of conduction and myocardial cells. Whereas calcium is the main electrolyte responsible for pacemaker cell depolarization, sodium and potassium are the main electrolytes responsible for depolarization of myocardial cells and cells dedicated to conduction of impulses.

The control unit 12 may also compare one or more MAP signals or characteristics thereof to an electrocardiogram signal to assess or verify the quality of the signal information received. In particular, the timing of a MAP signal or waveform may be compared to a P, QRS, and/or T-wave segment of a surface electrogram or electrocardiogram. For example, the extent that a repolarization segment of a MAP signal coincides with the repolarization indication of the T-wave of an electrocardiogram can be used to assess the quality of a MAP signal.

The processed or computed metrics of an obtained MAP signal may be compared to expected or predetermined baseline or threshold values, or may be compared to surrounding population values or measurements taken within a designated tissue area. Differences between obtained MAP signal metrics and expected or surrounding values or measurements may be graphically displayed by the system 10 to graphically indicate or map abnormally-behaving regions (which may indicate underlying ion channel irregularities, for example) to aid in diagnosis or treatment. Such ion channel irregularities may include, for example, long QT syndrome (which may be indicated by an extended plateau on a MAP signal exceeding a designated threshold) or Burgada syndrome (which may be indicated by a "saddlebag" or dip in the plateau of the MAP signal).

The graphical indication may include spatial and/or temporal presentations to indicate characteristics across a plurality of locations, or metrics and analysis for a substantially single location over time, respectively. For example, referring again to FIG. 3, the first and second images 46, 50 may include an anatomical rendering of a tissue region or structure of the patient 14. Information resulting from the analysis of the MAP signal metrics may be graphically overlaid or integrated into the first and/or second images 46, 50 at a location on the images corresponding to the location where the MAP signal was taken in the patient, and may also include a time stamp or other temporal indication. The location information of the MAP signal may be obtained through tracking the medical device 20, for example, used to record or otherwise obtain the MAP signal. Location or position information regarding the medical device 20, and thus the MAP signal, may be obtained through medical device tracking systems and methodologies as known in the art.

Figure 8:
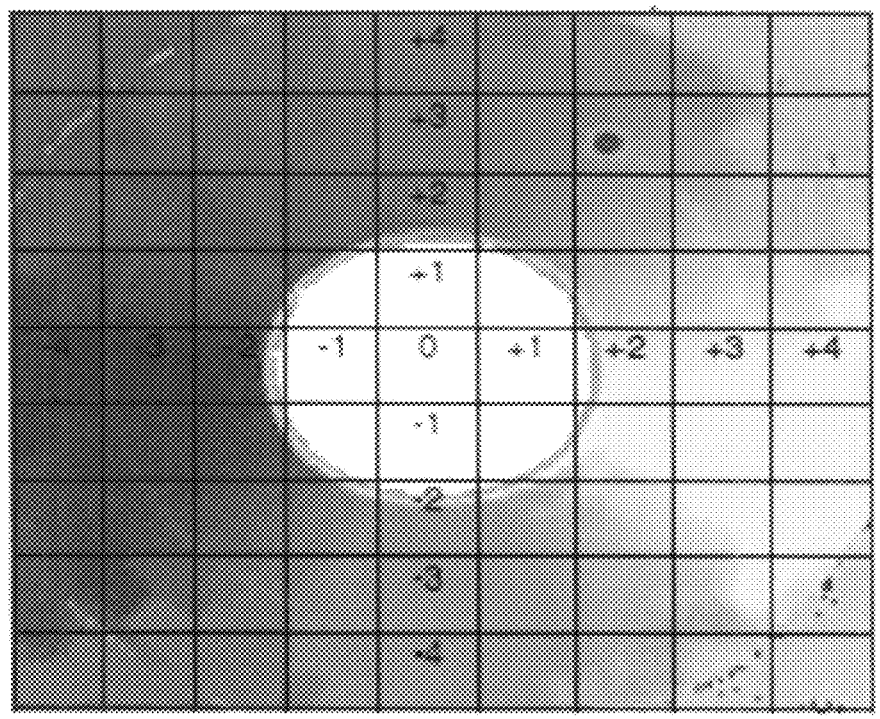
FIG. 8 is an illustration of a graphical identification scheme for a plurality of measured values.
Figure 9:
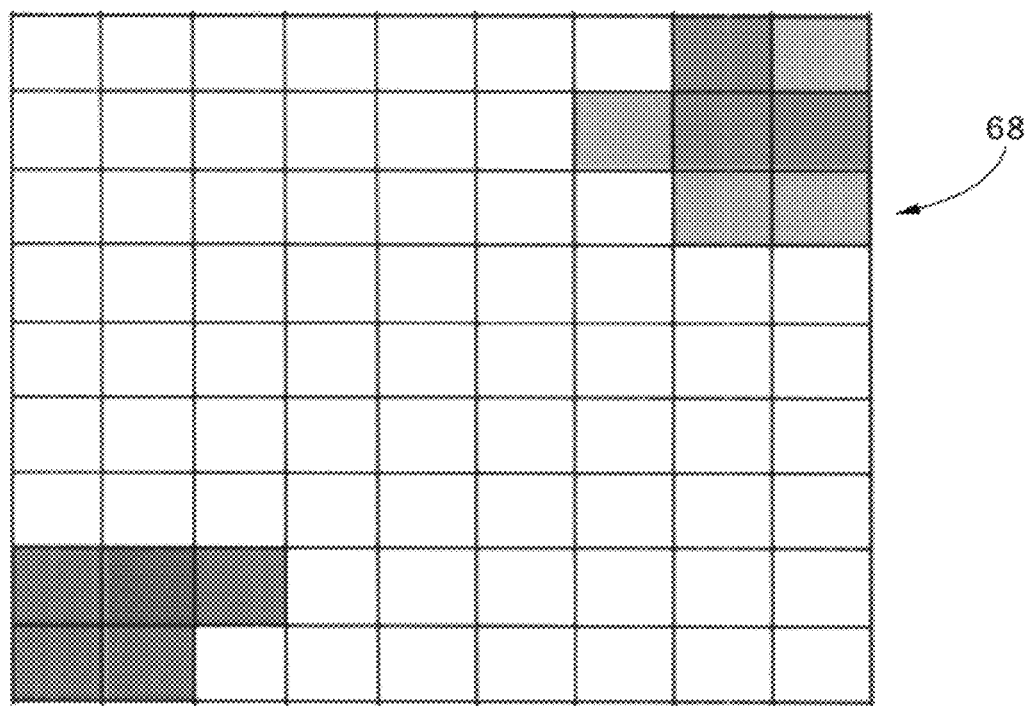
FIG. 9 is an illustration of an image including electrophysiological indicators.

The calculated or processed values of the MAP signal characteristics may be assigned or correlated to a graphical indicator to emphasize differences in measured or processed values from expected values on the display 38. For example, FIG. 8 illustrates a color scheme that can be used to graphically distinguish variations from an expected value (e.g., 0,0) along two different axes. For MAP signal values, the axes may represent variations in voltage and time, respectively. These color variations can then be shown on segments 68 of the first and/or second images that have been mapped with electrophysiological readings or measurements. As shown in FIG. 3, the mapped segment 68 graphically shows areas or sectors having deviations from expected values directly on the anatomical rendering, while values or metrics of MAP signals that are within expected ranges are shown as a base color. The mapped segment 68 is shown in a substantially planar form in FIG. 9 for reference. The calculated values and/or deviations may be assigned to graphical indicators on a spatial or temporal basis. For example, a mapped, displayed region may indicate different values (i.e., different colors) from one location to the next, or may include assigned graphical indicators or colors based on a deviation or change in a measured value form a single location over time (i.e., a base color indicates little change over time, while another color or marker indicates significant change over time).

The system 10 may also provide a visual or graphic indication suggesting or recommending locations for treatment or further action based at least in part on the measured and/or processed metrics of the MAP signal. For example, should the MAP single analysis include a plurality of metrics or characteristics deviating from the expected values, the control unit 14 and/or display could generate a "flag" or "hot spot" indication (in addition to the graphical indicator representing the measured deviation) for further action. The criteria for generating such an alert or visual marker on the display could include an analysis of one or more of the measured MAP characteristics as compared to clinically expected values or patient-specific data. A threshold for generating such an alert may include, for example, that at least three metrics of the MAP signal exceed expected values (i.e., upstroke velocity, plateau duration, maximum voltage, etc.).

Though the mapped segment is shown in FIG. 3 as a portion of the first image 46, it is contemplated that an entire anatomical region and its associated imaged rendering may be mapped for electrophysiological activity and MAP metrics. In addition, though the mapped segment 68 is shown as including a plurality of square-like sectors, it is contemplated that the rendered image may be divided into a myriad of different groupings to indicate the desired MAP signal parameters or assigned values. For example, a three-dimensional rendering may include a plurality of triangles intersecting at vertices indicating changes in the tissue topography, with the resulting electrophysiological assessment being assigned or attributed to an individual triangle on an image. Further, while the description above describes data being mapped to a three-dimensional model, data may be mapped to any map including, but not limited to, a two- or three-dimensional, static or time-varying image or model.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of displaying electrophysiological information; comprising:
   obtaining a three-dimensional rendering of an anatomical region;
   obtaining a monophasic action potential signal with a medical device from at least a portion of the anatomical region;
   obtaining an electrocardiogram signal from at least a portion of the anatomical region;
   calculating a value associated with a depolarization segment of the monophasic action potential signal;
   displaying a graphical indicator of the value on the rendering of the anatomical region;
   comparing at least a portion of the monophasic action potential signal to at least a portion of the electrocardiogram signal and assessing the contact between the medical device and the anatomical region based at least in part on the comparison; and
   generating an alert based at least in part on the comparison.

2. The method of claim 1, wherein the three-dimensional rendering is generated using electric potential-based navigation.

3. The method of claim 1, wherein the electric potential-based navigation includes tracking one or more electrodes in three-dimensional space in proximity to the anatomical region.

4. The method of claim 1, wherein calculating the value associated with the depolarization segment includes calculating a time duration.

5. The method of claim 1, wherein calculating the value associated with the depolarization segment includes calculating an upstroke velocity.

6. The method of claim 1, wherein calculating the value associated with the depolarization segment includes:
   calculating a maximum amplitude value; and
   calculating a time duration for the monophasic action potential signal to recede to a predetermined percentage of the maximum amplitude value.

7. The method of claim 1, further comprising identifying a tissue structure based at least in part on the calculated value.

8. The method of claim 1, wherein obtaining the monophasic action potential signal includes contacting the anatomical region with a medical device, and the generating an alert comprises generating a contact status indication.

9. The method of claim 1, wherein comparing at least a portion of the monophasic action potential signal to the electrocardiogram signal includes comparing a portion of the monophasic action potential signal to a T-wave portion of the electrocardiogram signal.

10. The method of claim 1, wherein the graphical indicator includes a color assigned to the value.

11. The method of claim 1, wherein the anatomical region includes at least a portion of a heart.

12. The method of claim 1, further comprising generating a graphical treatment indicator on the rendering based at least in part on the calculated value, the graphical treatment indicator providing a recommended treatment location.

13. A method of mapping electrophysiological information, comprising:
   receiving imaging information for a tissue region;
   receiving a monophasic action potential signal from the tissue region using a medical device with one or more mapping electrodes;
   receiving an electrocardiogram signal from the tissue region using the medical device;
   assigning a value corresponding to a depolarization segment of the monophasic action potential signal;
   receiving location information associated with the monophasic action potential signal;
   generating an image based on the imaging information, the assigned value, and the location information; and
   comparing at least a portion of the monophasic action potential signal and at least a portion of the electrocardiogram signal and assessing the quality of the monophasic action potential signal based at least in part on the comparison.

14. The method of claim 13, wherein receiving a monophasic action potential signal from the tissue region includes obtaining a monophasic action potential signal with a medical device proximate to the tissue region.

15. The method of claim 14, wherein receiving location information associated with the monophasic action potential signal includes obtaining location information of the medical device.

16. The method of claim 13, wherein generating an image includes displaying a three-dimensional rendering of the tissue region.

17. The method of claim 16, wherein the rendering includes a color variation indicating the assigned value at a location on the rendering corresponding to the received location information.

18. The method of claim 13, wherein receiving imaging information for a tissue region includes receiving three-dimensional electric potential information.

19. The method of claim 13, wherein the rendering includes a color variation indicating a suggested location for treatment.

20. A medical system, comprising:
   a display;
   a control unit in communication with the display, the control unit programmed to:
      receive a monophasic action potential signal,
      receive three-dimensional location information associated with the monophasic action potential signal,
      receive an electrocardiogram signal;
      calculate a value corresponding to a depolarization segment of the monophasic action potential signal;
      generate an image based on the three-dimensional location information and the calculated value; and compare at least one of a timing and a waveform of the monophasic action potential signal to at least one of a P-wave segment, a QRS complex, and a T-wave segment of the electrocardiogram signal and assess the quality of the monophasic action potential signal based at least in part on the comparison.

21. The system of claim 20, wherein the control unit is programmed to:
generate an alert based at least in part on the comparison between the at least a portion of the monophasic action potential signal and the at least a portion of the electrocardiogram signal.

22. The system of claim 20, further comprising a medical device in communication with the control unit, the medical device including a plurality of electrodes.

23. The system of claim 20, further comprising an image acquisition device in communication with the control unit.

* * * * *

UNITED STATES PATENT AND TRADEMARK OFFICE
CERTIFICATE OF CORRECTION

| | |
|---|---|
| PATENT NO. | : 10,039,502 B2 |
| APPLICATION NO. | : 13/084853 |
| DATED | : August 7, 2018 |
| INVENTOR(S) | : Mark T. Stewart et al. |

It is certified that error appears in the above-identified patent and that said Letters Patent is hereby corrected as shown below:

On the Title Page

In (75) in the Inventor name, replace "Giles" with -- Gilles --.

Signed and Sealed this
Nineteenth Day of March, 2019

Andrei Iancu
*Director of the United States Patent and Trademark Office*